US005895810A

United States Patent [19]

Light et al.

[11] Patent Number: 5,895,810
[45] Date of Patent: Apr. 20, 1999

[54] STABLE POLYMERIZED HEMOGLOBIN AND USE THEREOF

[75] Inventors: William R. Light, Natick; Maria S. Gawryl, Charlestown; Anthony J. Laccetti, North Andover, all of Mass.

[73] Assignee: Biopure Corporation, Cambridge, Mass.

[21] Appl. No.: 08/487,288

[22] Filed: Jun. 7, 1995

Related U.S. Application Data

[63] Continuation-in-part of application No. 08/458,916, Jun. 2, 1995, Pat. No. 5,840,852, which is a continuation of application No. 08/409,337, Mar. 23, 1995, Pat. No. 5,854,209.

[51] Int. Cl.[6] .................................................. C07K 14/805
[52] U.S. Cl. ............................... 530/385; 530/402; 514/6
[58] Field of Search .................................. 514/6; 530/385, 530/402

[56] References Cited

U.S. PATENT DOCUMENTS

| Re. 34,271 | 6/1993 | Walder | 530/385 |
|---|---|---|---|
| 3,864,478 | 2/1975 | Bonhard | 424/101 |
| 4,001,200 | 1/1977 | Bonsen et al. | 260/112.5 |
| 4,136,093 | 1/1979 | Bonhard et al. | 260/112.5 R |
| 4,336,248 | 6/1982 | Bonhard et al. | 424/101 |
| 4,439,357 | 3/1984 | Bonhard et al. | 260/112 B |
| 4,473,496 | 9/1984 | Scannon | 260/112 B |
| 4,529,719 | 7/1985 | Tye | 514/6 |
| 4,584,130 | 4/1986 | Bucci et al. | 260/112 B |
| 4,598,064 | 7/1986 | Walder | 514/6 |
| 4,600,531 | 7/1986 | Walder | 530/385 |
| 4,826,811 | 5/1989 | Sehgal et al. | 514/6 |
| 4,857,636 | 8/1989 | Hsia | 530/385 |
| 4,861,867 | 8/1989 | Estep | 530/385 |
| 4,900,780 | 2/1990 | Cerny | 525/54.1 |
| 4,920,194 | 4/1990 | Feller et al. | 530/385 |
| 5,051,353 | 9/1991 | Stratton et al. | 435/2 |
| 5,084,558 | 1/1992 | Rausch et al. | 530/385 |
| 5,114,932 | 5/1992 | Runge | 514/58 |
| 5,128,452 | 7/1992 | Hai et al. | 530/385 |
| 5,189,146 | 2/1993 | Hsia | 530/385 |
| 5,194,590 | 3/1993 | Sehgal et al. | 530/385 |
| 5,234,903 | 8/1993 | Nho et al. | 514/6 |
| 5,250,665 | 10/1993 | Kluger et al. | 530/385 |
| 5,264,555 | 11/1993 | Shorr et al. | 530/385 |
| 5,296,465 | 3/1994 | Rausch et al. | 514/6 |

FOREIGN PATENT DOCUMENTS

| WO88/03408 | 5/1988 | WIPO . |
| WO89/12456 | 12/1989 | WIPO . |

OTHER PUBLICATIONS

J.C. Cabacungan et al., "Amine Boranes as Alternative Reducing Agents for Reductive Alkylation of Proteins," *Analytical Biochemistry* 124:272–278 (1982).

*Primary Examiner*—Cecilia J. Tsang
*Assistant Examiner*—Anish Gupta
*Attorney, Agent, or Firm*—Hamilton, Brook, Smith & Reynolds, P.C.

[57] ABSTRACT

The present invention relates to a composition of matter comprising a stable polymerized hemoglobin solution, useful for forming blood-substitutes, and to a method for forming said stable polymerized hemoglobin solution. The stable polymerized hemoglobin solution, and derived blood-substitutes, of this invention comprise polymerized hemoglobin and a sulfhydryl compound, both in solution, wherein the sulfhydryl compound stabilizes the polymerized hemoglobin.

The method of this invention comprises deoxygenating hemoglobin in a hemoglobin solution and then mixing the deoxygenated hemoglobin with a sulfhydryl compound to form an oxidation-stabilized, deoxygenated hemoglobin solution. Subsequently, the oxidation-stabilized deoxygenated hemoglobin solution is mixed with a cross-linking agent to form a polymerization reaction mixture, which is then polymerized to form a stable polymerized hemoglobin solution.

24 Claims, 1 Drawing Sheet

STABLE POLYMERIZED HEMOGLOBIN AND USE THEREOF

RELATED APPLICATIONS

This application is a Continuation-in-Part of U.S. patent application Ser. No. 08/458,916 filed on Jun. 2, 1995, entitled "METHOD FOR PRODUCING ULTRAPURE STABLE POLYMERIZED HEMOGLOBIN BLOOD-SUBSTITUTE," by Carl W. Rausch, et al., now U.S. Pat. No. 5,840,852 which is a Continuation of U.S. patent application Ser. No. 08/409,337, filed Mar. 23, 1995, now U.S. Pat. No. 5,854,209 the teachings of which are incorporated herein by reference.

BACKGROUND OF THE INVENTION

There exists a need for a blood-substitute to treat or prevent hypoxia resulting from blood loss inter alia (e.g. from acute hemorrhage or during surgical operations), resulting from anemia (e.g., pernicious anemia or sickle cell anemia), or resulting from shock (e.g. volume deficiency shock, anaphylactic shock, septic shock or allergic shock).

The use of blood and blood fractions as in these capacities as a blood-substitute is fraught with disadvantages. For example, the use of whole blood often is accompanied by the risk of transmission of hepatitis-producing viruses and AIDS-producing viruses which can complicate patient recovery or result in patient fatalities. Additionally, the use of whole blood requires blood-typing and cross-matching to avoid immunohematological problems and interdonor incompatibility.

Human hemoglobin, as a blood-substitute, possesses osmotic activity and the ability to transport and transfer oxygen, but it has the disadvantage of rapid elimination from circulation by the renal route and through vascular walls, resulting in a very short, and therefore, a typically unsatisfactory half-life. Further, human hemoglobin is also frequently contaminated with toxic levels of endotoxins, bacteria and/or viruses.

Non-human hemoglobin suffers from the same deficiencies as human hemoglobin. In addition, hemoglobin from non-human sources is also typically contaminated with proteins, such as antibodies, which could cause an immune system response in the recipient.

Previously, at least four other types of blood-substitutes have been utilized, including perfluorochemicals, synthesized hemoglobin analogues, liposome-encapsulated hemoglobin, and chemically-modified hemoglobin. However, many of these blood-substitutes have typically had short intravascular retention times, being removed by the circulatory system as foreign substances or lodging in the liver, spleen, and other tissues. Also, many of these blood-substitutes have been biologically incompatible with living systems.

In spite of the recent advances in the preparation of cross-linked hemoglobin blood-substitutes, the need has continued to exist for a blood-substitute which can be stored for longer periods at ambient temperatures without significant degradation, such as through dimer formation or through methemoglobin formation. In addition, the needed blood-substitute should also have a lower oxygen affinity, an oncotic activity equivalent to that of whole blood, and a good intravascular retention time.

SUMMARY OF THE INVENTION

The present invention relates to a composition of matter comprising a stable polymerized hemoglobin solution, useful for forming blood-substitutes, and to a method for forming said stable polymerized hemoglobin solution. The stable polymerized hemoglobin solution, and derived blood-substitutes, of this invention comprise polymerized hemoglobin and a sulfhydryl compound, both in solution, wherein said sulfhydryl compound stabilizes said polymerized hemoglobin.

The method of this invention comprises deoxygenating hemoglobin in a hemoglobin solution and then mixing the deoxygenated hemoglobin with a sulfhydryl compound to form an oxidation-stabilized, deoxygenated hemoglobin solution. Subsequently, the oxidation-stabilized deoxygenated hemoglobin solution is mixed with a cross-linking agent to form a polymerization reaction mixture, which is then polymerized to form a stable polymerized hemoglobin solution.

The advantages of this stable polymerized hemoglobin solution are that the blood-substitutes, derived therefrom, have a greatly increased storage time at ambient temperatures of over two years or more, a relatively low oxygen affinity, an increased intravascular retention time, and a suitable oncotic pressure.

DETAILED DESCRIPTION OF THE INVENTION

Figure 1:
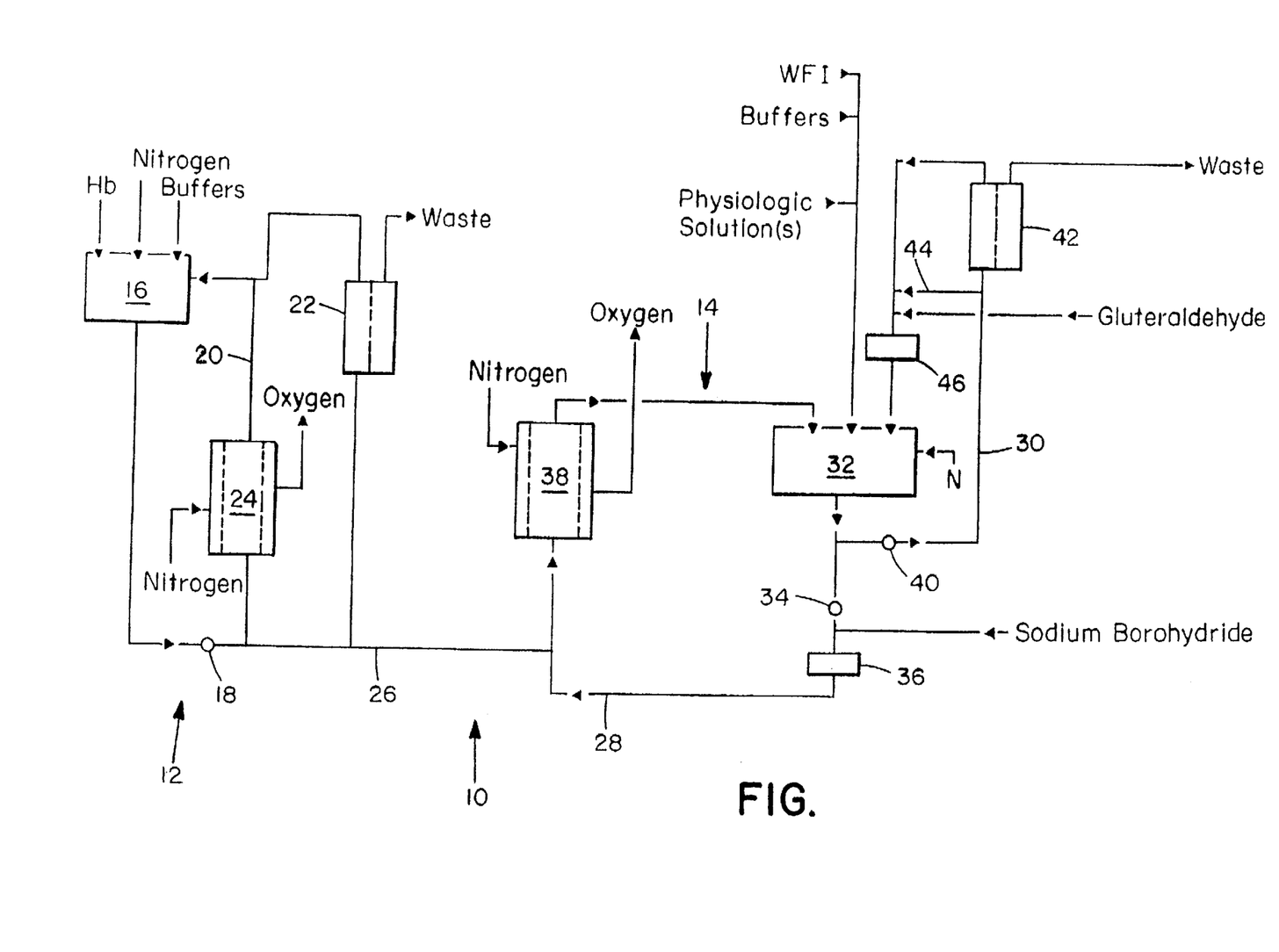
The FIGURE represents a schematic flow diagram of a method for producing the stable polymerized hemoglobin solution, and a subsequently derived blood-substitute, of the present invention.

In the method of invention, portions of the components for the process for preparing stable polymerized hemoglobin solutions, and blood-substitutes derived therefrom, are sufficiently sanitized while performing this process to produce a sterile product. Further, portions of components, that are exposed to the process stream, are usually fabricated or clad with a material that will not react with or contaminate the process stream. Such materials can include stainless steel and other steel alloys, such as Inconel.

A blood-substitute, as defined herein, is a hemoglobin-based oxygen carrying composition which is capable of transporting and transferring oxygen to at least vital organs and tissues and can maintain sufficient intravascular oncotic pressure.

Stable polymerized hemoglobin (Hb), as defined herein, is a hemoglobin-based oxygen carrying composition which does not substantially increase or decrease in molecular weight distribution and/or in methemoglobin content during storage periods at suitable storage temperatures for periods of over one year or more, and preferably for periods of over two years or more, when stored in a low oxygen environment. Suitable storage temperatures for storage of more than one year were between about 0° C. and about 40° C. The preferred storage temperature range is between about 0° C. and about 25° C.

A suitable low oxygen environment is defined as the cummulative amount of oxygen in contact with the blood-substitute, over a period of at least two years, which will result in a methemoglobin concentration of less than about 15% by weight in the blood substitute. The cummulative amount of oxygen includes oxygen inleakage into the blood0substitute packaging and the original oxygen content of the blood-substitute and packaging.

A high molecular weight Hb polymer chain, as defined herein, is a Hb polymer chain with a molecular weight above about 500,000 Daltons. Furthermore, polymerized hemoglobin, as defined herein, is hemoglobin that is intermolecularly cross-linked to form polymer chains and/or intramolecularly cross-linked to stabilize the hemoglobin against dimer formation.

Hemoglobin suitable for Hb solutions of this invention can be derived from new, old or outdated blood from humans and/or other mammals, such as cattle, pigs and sheep. In addition, transgenically-produced hemoglobin, such as the transgenic Hb described in *BIO/TECHNOLOGY*, 12: 55–59 (1994), and recombinantly produced hemoglobin, such as the recombinantly produced hemoglobin described in *Nature*, 356: 258–260 (1992), are also suitable for Hb solutions of this invention. The composition of Hb solutions preferred for use in the method of invention are sterile solutions having less than 0.5 endotoxin units/ml, a methemoglobin content that will not result in a significant reduction in oxygen transport/transfer capacity, a total hemoglobin concentration between about 2 to about 20 g Hb/dl, a physiologic pH and a chloride ion concentration of less than 35 meq/l. In an even more preferred embodiment, the Hb solution has a total hemoglobin concentration between about 12 to about 14 g Hb/dl.

The term "endotoxin" refers to the cell-bound lipopolysaccharides produced as a part of the outer layer of bacterial cell walls, which under many conditions are toxic. An endotoxin unit (EU) has been defined, by the United States Pharmacopeial Convention of 1983, page 3013, as the activity contained in 0.1 nanograms of U.S. reference standard lot EC-5. One vial of EC-5 contains 10,000 Eu.

Sterile is as defined in the art, specifically, that the solution meets United States Pharmacopeia requirements for sterility provided in USP XXII, Section 71, pages 1483–1488.

An example of a physiologic pH is a pH between about 7.2 and about 7.9 at 18–22° C. A preferred physiologic pH for a blood-substitute is a pH between about 7.6 and about 7.9 at 18–22° C.

Typically, a methemoglobin content which will not result in a significant reduction in oxygen delivery capacity, is a methemoglobin content of less than or equal to about 25%. It is preferred that methemoglobin content be less than about 15%. In an even more preferred embodiment, the methemoglobin content in a Hb solution is less than or equal to about 10%.

Examples of Hb solutions, suitable for the method of invention, include solutions of Hb elute described in Examples 1 and 2 herein, in U.S. Pat. No. 5,296,465, and in copending U.S. patent application Ser. No. 08/484,775, Attorney Docket No. BP94-03A2, filed Jun. 7, 1995, the teachings of which are incorporated herein by reference.

In the method of the present invention, a Hb solution is deoxygenated prior to polymerization to form a deoxygenated Hb solution (hereinafter deoxy-Hb). In one embodiment, the Hb solution is deoxygenated by gas exchange of oxygen with an inert gas across a phase membrane. Such inert gases include, for example, nitrogen, argon and helium. It is understood that other means for deoxygenating a solution or hemoglobin, which are known in the art, can be used to deoxygenate the Hb solution. Such other means, can include, for example, nitrogen purging of the Hb solution, chemical scavenging with reducing agents such as N-acetyl-L-cysteine (NAC), cysteine, sodium dithionite or ascorbate, or photolysis by light.

During deoxygenation, and subsequently throughout the method of this invention, the Hb is maintained in a low oxygen environment to minimize oxygen absorption by the Hb solution. Suitable low oxygen environments include, for example, environments which would result in an oxygenated Hb (oxyhemoglobin or $HbO_2$) content of less than about 20% in the Hb solution.

Deoxygenation is continued until a low oxygen concentration is achieved which is suitable to limit significant methemoglobin formation and which results in a large proportion of the Hb molecules having a structural configuration that will result in a low oxygen affinity when the Hb is cross-linked, thereby enhancing the oxygen delivery capacity of the hemoglobin. Typically, deoxygenation continues until $HbO_2$ concentration is less than about 20%, and preferably less than about 10%.

The deoxy-Hb is then mixed with a suitable deoxygenated storage buffer and a cross-linking agent. It is understood that the storage buffer and the cross-linking can be added to the deoxy-Hb concurrently, or the cross-linking agent can be added to the deoxy-Hb after adding the storage buffer. It is preferred that the storage buffer and cross-linking agent be added to the deoxy-Hb sequentially.

A suitable deoxygenated storage buffer contains an amount of a non-toxic sulfhydryl compound suitable to stabilize the deoxygenated Hb solution against oxidation to form oxidation-stabilized deoxy-Hb. Examples of suitable sulfhydryl compounds include N-acetyl-L-cysteine, D,L-cysteine, glutathione, γ-glutamyl-cysteine, 2,3-dimercapto-1-proponal, thioglycolate, 1,4-butanedithiol and other biologically compatible sulfhydryl compounds. The functions of the sulfhydryl compound include deoxygenating oxygenated Hb remaining in the deoxy-Hb, reducing methemoglobin remaining in the deoxy-Hb, maintaining the deoxy-Hb (and a final Hb blood-substitute product) in an oxidation-stabilized (i.e., deoxygenated) state at room temperature by oxygen scavenging, and facilitating optimal Hb polymerization to preferentially form modified tetrameric Hb.

Modified tetrameric Hb, as defined herein, is tetrameric Hb which has been intramolecularly cross-linked to preclude significant dissociation of the Hb tetramers into Hb dimers.

The amount of a sulfhydryl compound mixed with the deoxy-Hb is an amount high enough to increase intramolecular cross-linking of Hb during polymerization, resulting in increased formation of modified tetrameric Hb, and an amount low enough not to substantially decrease intermolecular cross-linking of Hb molecules, due to a high ionic strength. Typically, about one mole of sulfhydryl functional groups (—SH), contained in a sulfhydryl compound, is needed to stabilize from about 0.25 to about 5 moles of deoxygenated Hb.

The pH and oxygen content of the storage buffer should be suitable to ensure that the oxidation-stabilized deoxy-Hb will have a pH suitable to balance Hb polymerization and methemoglobin formation, preferably from 7.6 to about 7.9 pH units, and an oxygen content of less than about 20% $HbO_2$ after stabilization, preferably ≦10% $HbO_2$, also limiting methemoglobin formation.

In one embodiment, the storage buffer also contains a buffer to stabilize pH in order to keep the ionic strength of the deoxy-Hb low enough not to significantly interfere with intermolecular cross-linking during polymerization. Typically, the ionic strength of the oxidation-stabilized deoxy-Hb is less than about 50 mOsm before polymerization.

In a preferred embodiment, an amount of an N-acetyl cysteine (NAC) storage buffer is added to the deoxy-Hb such that, before polymerization, the oxidation-stabilized deoxy-Hb contains from about 0.003% to about 0.3% NAC, by weight.

In a more preferred embodiment, an amount of an NAC storage buffer is added to the deoxy-Hb such that, before polymerization, the oxidation-stabilized deoxy-Hb contains from about 0.03% to about 0.3% NAC by weight, or an equivalent mole percent for other sulfhydryl compounds.

In an even more preferred embodiment, the oxidation-stabilized deoxy-Hb contains between about 0.05% and about 0.2% by weight NAC before initiating polymerization.

In one embodiment, the storage buffer is filtered before mixing with the deoxy-Hb. A suitable filter for a storage buffer is capable of depyrogenating the buffer, typically a 10,000Dalton, or less, filter or membrane. Examples of a suitable storage buffer filter include Millipore Helicon, Cat #CDUF050G1 or AG Technology Maxcell, Cat #UFP-10-C-75 depyrogenating filters having exclusion limits of 10,000 Daltons.

An example of a suitable storage buffer is described in Example 1.

The oxidation-stabilized deoxy-Hb is then mixed with a suitable cross-linking agent to form a polymerization reaction mixture. The polymerization reaction mixture is then exposed to conditions suitable to polymerize the oxidation-stabilized deoxy-Hb to form polymerized hemoglobin (poly (Hb)). It is preferred that the cross-linking agent and the oxidation-stabilized deoxy-Hb are mixed by a means for mixing with low shear. Suitable low-shear mixing means include, for example, static mixers and low speed marine blade impellers.

Examples of suitable cross-linking agents include polyfunctional agents, such as glutaraldehyde; succindialdehyde; activated forms of polyoxyethylene and dextran; α-hydroxy aldehydes such as glycolaldehyde, N-maleimido-6-aminocaproyl-(2'-nitro, 4'-sulfonic acid)-phenyl ester, m-maleimido-benzoic acid-N-hydroxysuccinimide ester, succinimidyl 4-(N-maleimidomethyl)cyclohexane-1-carboxylate, sulfosuccinimidyl 4-(N-maleimidomethyl) cyclohexane-1-carboxylate, m-maleimidobenzoyl-N-hydroxysuccinimide ester, m-maleimidobenzoyl-N-hydroxysulfosuccinimide ester, N-succinimidyl(4-iodoacetyl)aminobenzoate, sulfosuccinimidyl(4-iodoacetyl) aminobenzoate, succinimidyl 4-(p-maleimidophenyl) butyrate, sulfosuccinimidyl 4-(p-maleimidophenyl)butyrate, 1-ethyl-3-(3-dimethylaminopropyl)carbodiimide hydrochloride, N,N'-phenylene dimaleimide; and compounds belonging to the bis-imidate class, the acyl diazide class or the aryl dihalide class, among others.

A suitable amount of a cross-linking agent is that amount which will intramolecularly stabilize the Hb and form polymers of a size sufficient, through intermolecular bonding, to increase vascular retention. Typically, a suitable amount of a cross-linking agent is that amount wherein the molar ratios of cross-linking agent to Hb is in excess of about 2:1. A preferred molar ratio of cross-linking agent to Hb is between about 20:1 to about 40:1.

In one embodiment, conditions for polymerizing hemoglobin include heating the polymerization reaction mixture to a temperature which is high enough to cause some intramolecular Hb cross-linking and sufficiently low to prevent significant Hb denaturation. Typically the polymerization reaction mixture is heated to a temperature from about 25° C. to about 45° C. for approximately 2 to 6 hours. However, at least a portion of the polymerization reaction mixture will polymerize at temperatures below 25° C. Preferred polymerization conditions include heating said reaction mixture to about 40° C. to about 44° C. for approximately 4–6 hours.

Significant Hb intramolecular cross-linking will result during Hb polymerization due to the presence of a sulfhydryl compound, preferably N-acetyl cysteine, in the oxidation-stabilized deoxy-Hb. The sulfhydryl compound effects glutaraldehyde/Hb chemical bonding in a manner that at least partially inhibits the formation of high molecular weight Hb polymers and preferentially forms stabilized tetrameric Hb.

In yet another embodiment, such as wherein the cross-linking agent used is an aldehyde, the poly(Hb) formed is not stable until mixed with a suitable reducing agent to reduce less stable imine bonds in the poly(Hb) to form more stable ketimine bonds. Examples of suitable reducing agents include sodium borohydride, sodium cyanoborohydride, sodium dithionite, trimethylamine, t-butlyamine, morpholine borane or pyridine borane.

Prior to adding the reducing agent to the poly(Hb), the pH of the poly(Hb) is basified by adjusting pH to the alkaline range to preserve the reducing agent and to prevent hydrogen gas formation, which can denature proteins during reduction. In one embodiment, the pH is adjusted to a pH of about 10, or more.

The pH of the poly(Hb) is typically adjusted by diafiltering the poly(Hb) with a depyrogenated alkaline solution, preferably a buffer solution. In diafiltration, a diluting solution, such as a depyrogenated alkaline buffer solution, is added to the poly(Hb) while concurrently passing the poly (Hb) through a filtration unit wherein the retenate is polymerized Hb, while the filtrate comprises water and smaller molecular weight components. Diafiltration also removes at least a portion of excess cross-linking agent and other chemicals contained in the poly(Hb).

Alternatively, the pH of the poly(Hb)can be raised by adding an alkaline buffer to the poly(Hb).

In a more preferred embodiment the poly(Hb) is diafiltered with a depyrogenated, deoxygenated sodium borate buffer, having a pH of about 10.4 to about 10.6, wherein the buffer is added to the poly(Hb) at a rate approximately equivalent to the rate of fluid loss across the filtration unit from diafiltration. It is preferred that poly(Hb) diafiltration is continued until the volume of fluid lost through diafiltration is about three times the initial volume of the poly(Hb). Suitable filtration units for diafiltration of poly(Hb) typically have molecular weight cut-offs between about 50,000 and about 1,000 Daltons, with a preferred molecular weight cut-off of about 30,000 Daltons. Examples of suitable filtration units for diafiltration include Millipore Helicon, Cat #CDUF050G1 and Amicon S40Y30 depyrogenating filters having exclusion limits of 30,000 Daltons.

A suitable range of amounts of reducing agent, added to the poly(Hb), is an amount required to reduce the imine bonds in the poly(Hb) but low enough to permit removal from the stable poly(Hb). Typically, between about 5 to about 18 moles of reducing agent are added per mole of Hb tetramer (per 64,000 Daltons of Hb) within the poly(Hb).

A stable polymerized hemoglobin produced according to the method of this invention comprises a Hb solution wherein about 60% or more of the Hb is polymerized; less than about 40% is modified tetrameric Hb and unmodified tetrameric Hb (tetrameric Hb which is not intramolecularly cross-linked); and less than about 15% of the Hb is contained in high molecular weight Hb polymer chains, such as those above 500,000 Daltons.

In one embodiment, after waiting to ensure that substantially all of the imine bonds in the poly(Hb) are reduced, typically about an hour or longer, the stable poly(Hb) is then filtered until concentrating the stable poly(Hb) to a concentration of about 90 g Hb/l to about 130 g Hb/l. Filters suitable to concentrate the stable poly(Hb) typically include filters with sizes between about 60,000 Daltons to about 1,000 Daltons, or less.

To convert the stable poly(Hb) to a stable polymerized hemoglobin blood-substitute, the stable poly(Hb) must have physiologic pH and electrolyte levels. The pH and electrolyte concentration in the stable poly(Hb) are adjusted to physiologic levels by diafiltering the stable poly(Hb) with a non-toxic, depyrogenated, deoxygenated acidic solution having physiologic electrolyte levels and a pH between about 4 and about 6, and preferably with a pH of about 5. The stable poly(Hb) is diafiltered with the acidic solution until forming a stable polymerized hemoglobin blood-substitute having physiologic pH and electrolyte levels. Typically, the stable poly(Hb) is diafiltered with a volume of the acidic solution between about 6 to about 10 times the volume of the stable poly(Hb). Preferably, the acidic solution is a buffer solution.

In a preferred embodiment, the buffer solution also contains a non-toxic reducing agent, such as a sulfhydryl compound, to scavenge oxygen within, or leaking into, the stable blood-substitute. The most preferred reducing agent is NAC.

In an even more preferred embodiment, wherein the Hb blood-substitute is used as a blood-substitute in humans and possibly for other mammals, the stable blood-substitute is purified by removing non-polymerized Hb, specifically modified tetrameric Hb, unmodified tetrameric Hb and dimeric Hb, from the poly(Hb). The Hb blood-substitute is diafiltered across a purification filter with a non-toxic, depyrogenated, deoxygenated solution having a physiologic pH and physiologic levels of electrolytes. Diafiltration continues until the stable blood-substitute contains less than about 10% modified tetrameric Hb and unmodified tetrameric Hb species by gel permeation chromatography (GPC) when run under dissociating conditions. A suitable purification filter typically has a molecular weight cutoff between about 50,000 Daltons and about 120,000 Daltons, with a preferable molecular weight cutoff of about 100,000 Daltons.

In one embodiment to enhance the diafiltration process, prior to diafiltration of the Hb blood-substitute to remove non-polymerized Hb, the Hb blood-substitute is diluted to a concentration of between about 20 g Hb/l to about 60 g Hb/l with a non-toxic, depyrogenated, deoxygenated solution having physiologic electrolyte levels and an acidic or physiologic pH.

One acceptable method for purifying a stable polymerized hemoglobin solution to establish physiologic conditions and also to remove non-polymerized Hb is described in co-pending U.S. patent application Ser. No. 08/484,775.

Following removal of substantial amounts of non-polymerized Hb, the Hb blood-substitute is concentrated to a concentration suitable to transport and transfer oxygen as a blood-substitute, typically to a level between about 10 g Hb/l and about 250 g Hb/l, and preferably to a level between about 120 g Hb/l and about 140 g Hb/l. Suitable membranes for this purpose have a molecular weight cutoff of 10,000 to 100,000 Daltion, preferably 30,000 Daltons.

A stable polymerized hemoglobin blood-substitute produced according to the method of this invention typically meets the specifications provided in Table I and of Example 3. In addition, Hb blood-substitute produced according to this method for veterinary uses typically meets the specifications provided in Table II. Furthermore, Hb blood-substitute produced according to this method for human uses typically meets the specifications provided in Table III. In a more preferred embodiment, the concentration of tetrameric Hb in the blood-substitute is less than or equal to about 5%. In an even more preferred embodiment, the concentration of tetrameric Hb in the blood-substitute is about 0%.

This method for producing a stable polymerized hemoglobin blood-substitute is particularly useful in developing an ultrapure stable polymerized hemoglobin blood-substitute as described in co-pending U.S. patent application Ser. No. 08/484,775.

TABLE I

| PARAMETER | SPECIFICATIONS |
| --- | --- |
| pH (18–22° C.) | physiologically acceptable pH |
| Endotoxin | physiologically accptable |
| Sterility Test | Meets Test |
| Phospholipids* | <3.3 nm/ml |
| Total Hemoglobin | 10–250 g/dl |
| Methemoglobin | <15% |
| Oxyhemoglobin | <10% |
| Sodium, Na$^+$ | Physiologically acceptable |
| Potassium, K$^+$ | |
| Chloride, CL$^-$ | |
| Calcium, Ca$^{++}$ | |
| Total Elemental Boron | |
| Glutaraldehyde | Physiologically acceptable |
| N-acetyl-L-cysteine | Physiologically acceptable |
| M. W. > 500,000 | ≤15% |
| M. W. ≤ 65,000 | ≤40% |
| Particulate Content ≥ 10 μ | <12/ml |
| Particulate Content ≥ 25 μ | <2/ml |

*measured in Hb before polymerization

TABLE II

| PARAMETER | SPECIFICATIONS |
| --- | --- |
| pH (18–22° C.) | physiologically acceptable pH |
| Endotoxin | <0.5 EU/ml |
| Sterility Test | Meets Test |
| Phospholipids* | <3.3 nm/mL |
| Total Hemoglobin | 12.0–14.0 g/dL |
| Methemoglobin | <15% |
| Oxyhemoglobin | ≤10% |
| Sodium, Na$^+$ | 145–160 mM |
| Potassium, K$^+$ | 3.5–5.5 mM |
| Chloride, Cl$^-$ | 105–120 mM |
| Calcium, Ca$^{++}$ | 0.5–1.5 mM |
| Total Elemental Boron | <10 ppm |
| Osmolality | 290–310 mOsm |
| Glutaraldehyde | <3.5 μg/ml |
| N-acetyl-L-cysteine | <0.2% |
| M. W. > 500,000 | ≤15% |
| Unmodified Tetramer | ≤5% |
| Particulate Content ≥ 10 μ | <12/mL |
| Particulate Content ≥ 25 μ | <2/mL |

*measured in Hb before polymerization

TABLE III

| PARAMETER | SPECIFICATIONS |
| --- | --- |
| pH (18–22° C.) | Physiologically acceptable pH |

TABLE III-continued

| PARAMETER | SPECIFICATIONS |
|---|---|
| Endotoxin | <0.5 EU/ml |
| Sterility Test | Meets Test |
| Phospholipids[a] | <3.3 nm/ml |
| Total Hemoglobin | 12.0–14.0 g/dl |
| Methemoglobin | <15% |
| Oxyhemoglobin | ≦10% |
| Sodium, $Na^+$ | 145–160 mM |
| Potassium, $K^+$ | 3.5–5.5 mM |
| Chloride, $Cl^-$ | 105–120 mM |
| Calcium, $Ca^{++}$ | 0.5–1.5 mM |
| Total Elemental Boron | ≦10 ppm |
| Osmolality | 290–310 mOsm |
| Glutaraldehyde | <3.5 μg/ml |
| N-acetyl-L-cysteine | ≦0.2% |
| M. W. > 500,000 | ≦15% |
| M. W. ≦ 65,000 | ≦10% |
| M. W. ≦ 32,000 | ≦5% |
| Particulate Content > 10 μ | <12/ml |
| Particulate Content > 25 μ | <2/ml |

[a]measured in Hb before polymerization

One embodiment of a system suitable for practicing the method of the present invention is illustrated in the FIGURE. This system, system 10, provides a means for substantially deoxygenating Hb and for polymerizing, while in a low oxygen environment, the deoxygenated hemoglobin (Hb), and then for reducing less stable imine bonds to produce a stable polymerized Hb solution, and for purifying the polymerized Hb solution to form a blood-substitute. System 10 includes Hb deoxygenation subsystem 12 and polymerization subsystem 14.

Hb deoxygenation subsystem 12 includes tank 16, pump 18, recirculation piping 20, ultrafilter 22, phase transfer membrane 24, and discharge line 26. Pump 18 takes suction on the Hb solution in tank 16 and discharges to either recirculation piping 20 or through discharge line 26. The flow of Hb solution through recirculation piping 20 then flows through ultrafilter 22 and/or phase transfer membrane 24, which are in parallel, and subsequently returns to tank 16.

Hb solution is added to tank 16 and then a buffer is directed, by means not shown, into the Hb solution in tank 16 to adjust the ionic strength of the concentrated Hb solution to enhance Hb deoxygenation.

It is preferred that the ionic strength of the Hb solution be adjusted to between about 150 meq/l and about 200 meq/l to reduce the oxygen affinity of the Hb in the Hb solution by the addition of a suitable buffer. Suitable buffers include buffers with a pH that will not result in significant denaturing of the Hb protein but will have an ionic strength sufficiently high to promote deoxygenation. Examples of suitable buffers include saline solutions with a pH range of 6.5 to about 8.9, and preferably with a pH of about 7.8. A preferred buffer is a 20 mM Tris, 1M NaCl buffer with a pH of about 8.9.

The resulting buffered Hb solution is then recirculated through ultrafilter 22, and returned to tank 16, to concentrate the Hb solution to form a concentrated Hb solution. In a preferred embodiment, concentration is complete when the concentration of Hb is between about 100 g Hb/l and about 120 g Hb/l. In one embodiment, the buffered Hb solution temperature is maintained at about 8° C. to about 12° C. during concentration. An example of an acceptable means for controlling Hb solution temperature in tank 16 is by cooling the outside of tank 16 through use of an ethylene glycol jacketed cooling system, not shown. A suitable ultrafilter for ultrafilter 22 includes, for example, a 10,000 Dalton to 30,000 Dalton ultrafilter. Examples of suitable ultrafilters include Millipore Helicon, Cat #CDUF050G1 and Amicon S40Y30 depyrogenating filters having exclusion limits of 10,000 Daltons.

In another embodiment, the Hb solution is concentrated prior to the buffer addition by recirculating of the Hb solution, by use of pump 18, from tank 16 through ultrafilter 22. Suitable Hb solution concentrations include, for example, concentrations between about 100 g Hb/l and 120 g Hb/l of Hb solution.

The concentrated Hb solution is then deoxygenated to form deoxy-Hb. In one embodiment, during deoxygenation the reconcentrated Hb solution is recirculated by pump 18 from tank 16, through phase transfer membrane 24, and then back to tank 16. Appropriate phase transfer membranes include, for example, a 0.05μ polypropylene microfilter (e.g., Hoechst-Celanese Corporation Cat #G-240/40) or a 0.05 μ microfilter (e.g., Hoechst-Celanese Corporation Cat #5PCM-108, 180 sq. ft.).

Concurrently, a counterflow of an inert gas is passed across phase transfer membrane 24. Suitable inert gases include, for example, nitrogen, argon and helium. Alternatively, a partial vacuum can be pulled on phase transfer membrane 24 in lieu of the inert gas flow, resulting in diffusion of oxygen from the Hb solution into the evacuated portion of the phase transfer membrane. Gas exchange (or diffusion) across phase transfer membrane 24 thereby strips oxygen out of the concentrated Hb. The flow rates of concentrated Hb solution and inert gas through phase transfer membrane 24 are at rates sufficient to deoxygenate the concentrated Hb solution. For example, when deoxygenating concentrated Hb solution across a 0.05μ polypropylene microfilter, flow rates of concentrated Hb solution and inert gas through the phase transfer membrane are typically about 8 to 12 lpm and about 40 to 60 lpm, respectively.

Deoxygenation is continued until the $pO_2$ of the reconcentrated Hb solution is reduced to the level where $HbO_2$ content in the Hb solution is less than or equal to about 20%. In a preferred embodiment, the Hb solution is deoxygenated until $HbO_2$ content is less than or equal to about 10%.

During deoxygenation the temperature of the Hb solution is typically maintained at a level that will balance the rate of deoxygenation against the rate of methemoglobin formation. An optimum temperature will result in less than about 5% methemoglobin content, and preferably less than about 2.5% methemoglobin content, while still deoxygenating the Hb solution. Typically, temperature of the Hb solution during deoxygenation is between about 19° C. and about 31° C.

The deoxy-Hb is then equilibrated with a depyrogenated, deoxygenated storage buffer, containing a sulfhydryl compound, such as NAC, to form a oxidation-stabilized deoxy-Hb. An acceptable storage buffer is depyrogenated by filtering the buffer, for example, through a 10,000 Dalton ultrafiltration membrane. In one embodiment, the storage buffer contains approximately 25–35 mM sodium phosphate buffer (pH 7.7–7.8), has a low oxygen content, such as less than about 50 torr $pO_2$, and also contains about 0.1% to about 0.3% by weight NAC. The storage buffer is added to the deoxy-Hb in tank 16 by means not shown.

Concurrently, the deoxy-Hb is diafiltered through recirculation from tank 16 by pump 18 through ultrafilter 22. In an alternate embodiment pump 18 is designed to allow pressurized flow through pump 18 while pump 18 is not operating. Suitable pumps include, for example, a rotary lobe sanitary pump (Albin Pump, Inc., Atlanta, Ga.; Model 325 or G+H Inc., Alfa-Laval, Kenosha, Wis., Model #732).

In another embodiment, the storage buffer is continuously added to tank 16 at a rate approximately equivalent to the fluid loss across ultrafilter 22 by maintaining the fluid level in tank 16 constant. In yet another embodiment, equilibration is continued until the volume of fluid lost through diafiltration across ultrafilter 22 is about three times the initial volume of the deoxy-Hb in tank 16. The volume of filtrate discharged from ultrafilter 22 can be measured by means known in the art, such as a drain line flow meter.

The oxidation-stabilized deoxy-Hb is subsequently transferred from Hb deoxygenation subsystem 12 through discharge line 26 by pressurizing tank 16 with an inert gas, such as nitrogen or argon. Polymerization subsystem 14 includes deoxygenation loop 28, concentration loop 30, and polymerization reactor 32. In deoxygenation loop 28, pump 34 recirculates fluid from polymerization reactor 32 through static mixer 36, and then through phase transfer membrane 38. Concentration loop 30 includes pump 40, which takes a suction from polymerization reactor 32 and recirculates fluid through ultrafilter 42, or through in-parallel bypass shunt 44, and then through static mixer 46. An example of an acceptable ultrafilter is a 30,000 Dalton ultrafiltration membrane (e.g., Millipore Helicon CDUF050LT or Amicon S40Y30). Suitable phase transfer membranes include, for example, 0.05µ polypropylene microfilters (e.g., Hoechst-Celanese Corporation Cat #5PCM-108, 180 sq.ft.).

Prior to transferring the oxidation-stabilized deoxy-Hb to polymerization subsystem 14, an appropriate amount of oxygen-depleted water-for-injection (WFI) is added to polymerization reactor 32 to purge polymerization subsystem 14 of oxygen to prevent oxygenation of oxidation-stabilized deoxy-Hb.

The term WFI is as classically defined in the pharmaceutical arts. For example, WFI is deionized, distilled water that meets U.S. Pharmacological Specifications for water-for-injection, as described in *Pharmaceutical Engineering*, 11, 15-23 (1991).

In one embodiment an appropriate amount of WFI is that amount which would result in a solution with a concentration of about 10 to about 120 g Hb/l, preferably about 37 g Hb/l to about 44 g Hb/l, when the oxidation-stabilized deoxy-Hb is added to polymerization reactor 32. The WFI is then recirculated by pump 34, throughout polymerization subsystem 28, to support deoxygenation of the WFI by flow through phase transfer membrane 38. A counterflow of a pressurized inert gas, such as nitrogen or argon, is directed across phase transfer membrane 38 to further deoxygenate the WFI. The flow rates of WFI and inert gas through phase transfer membrane 38 are at rates sufficient to deoxygenate the WFI. For example, when deoxygenating WFI across a 0.05µ polypropylene microfilter, flow rates of WFI and inert gas through the phase transfer membrane are typically about 18 to 20 lpm and 40 to 60 lpm, respectively.

After the $pO_2$ of the WFI in polymerization subsystem 28 is reduced to a sufficient level, such as less than about 2 torr $pO_2$, polymerization reactor 32 is blanketed with an inert gas, such as nitrogen or argon. The oxidation-stabilized deoxy-Hb is then transferred from Hb deoxygenation subsystem 12, by pressurizing tank 16 with an inert gas, through deoxygenation loop 28, and into polymerization reactor 32, which is concurrently blanketed with an appropriate flow of an inert gas. In one embodiment, the inert blanketing gas is provided by a flow of about 20 lpm of nitrogen or argon into the head space of polymerization reactor 32. The temperature of the oxidation-stabilized deoxy-Hb solution in polymerization reactor 32 is then raised to between about 25° C. and about 45° C., and preferably about 42° C., to initiate polymerization and is maintained at that temperature throughout polymerization by heat transfer means, not shown. An example of an acceptable heat transfer means for heating polymerization reactor 32 is a jacketed polymerization reactor heated by directing hot ethylene glycol through the jacket.

It is understood that other means for deoxygenating a solution, or hemoglobin, which are known in the art, can be used to deoxygenate a hemoglobin solution prior to or after transferring the hemoglobin solution to polymerization reactor 32. However, prior to polymerization, the deoxygenated Hb solution should contain a concentration of a suitable sulfhydryl compound with a concentration between about 0.003% and about 0.3%.

The oxidation-stabilized deoxy-Hb is then exposed to a suitable cross-linking agent for a temperature and time suitable to polymerize the oxidation-stabilized deoxy-Hb to form polymerized hemoglobin (poly(Hb)), such as about 25° C. to about 45° C. for approximately 2 to 6 hours. A preferred polymerization condition includes heating the oxidation-stabilized deoxy-Hb at about 42° C. for approximately 5 hours.

A suitable amount of the cross-linking agent is added to the oxidation-stabilized deoxy-Hb, which contains a sulfhydryl compound, such as NAC, through an orifice, not shown, while recirculating the oxidation-stabilized deoxy-Hb from polymerization reactor 32 through bypass shunt 44. The cross-linking agent and the oxidation-stabilized deoxy-Hb are then mixed by a means for mixing with low shear. A suitable low-shear mixing means includes static mixer 44. A suitable static mixer is, for example, a "KENICS" static mixer obtained from Chemineer, Inc.

In one embodiment, recirculating the oxidation-stabilized deoxy-Hb and the cross-linking agent through static mixer 44 causes turbulent flow conditions with generally uniform mixing of the cross-linking agent with the oxidation-stabilized deoxy-Hb thereby reducing the potential for forming pockets of deoxy-Hb containing high concentrations of cross-linking agent. Generally uniform mixing of cross-linking agent and deoxy-Hb reduces the formation of high molecular weight poly(Hb) and also permits faster mixing of the cross-linking agent and the deoxy-Hb during polymerization.

Furthermore, significant Hb intramolecular cross-linking will result during Hb polymerization as an effect of the presence of a sulfhydryl compound, such as NAC, upon the polymerization of Hb.

In another embodiment, a suitable amount of glutaraldehyde is between about 2 to about 100 grams of glutaraldehyde per kilogram of oxidation-stabilized deoxy-Hb, and preferably about 27 to about 32 grams of glutaraldehyde per kilogram of oxidation-stabilized deoxy-Hb. It is also preferred that the polymerization be conducted in a buffer having a chloride ion concentration of less than of equal to about 35 mM. An example of a suitable buffer is a 12 mM phosphate buffer with a pH of 7.8.

After polymerization, the temperature of the poly(Hb) in polymerization reactor 32 is typically reduced to a temperature that will inhibit any significant amount of further reactions with glutaraldehyde. Typically, temperature will be reduced to between about 5° C. and about 25° C., or preferably between about 18° C. to about 20° C. An example of an acceptable heat transfer means for cooling polymerization reactor 32 is a jacketed polymerization reactor which is cooled by ethylene glycol flow.

The poly(Hb) is then concentrated by recirculating the poly(Hb) through ultrafilter 42 until the concentration of the poly(Hb) is increased to between about 75 and about 85 g/l. A suitable ultrafilter is a 30,000 Dalton filter (e.g., Millipore Helicon, Cat #CDUF050LT).

Prior to adding a reducing agent to the poly(Hb), the pH of the poly(Hb) in polymerization reactor 32 is adjusted to about 10 pH units by diafiltering the poly(Hb) with a depyrogenated, deoxygenated sodium borate buffer, having a pH of about 10.4 to about 10.6, such as with a 12 mM sodium borate. The poly(Hb) is diafiltered by recirculating the poly(Hb) from polymerization reactor 32, by pump 40, through ultrafilter 42. In one embodiment the buffer is added to the poly(Hb) at a rate approximately equivalent to the rate of fluid loss across the ultrafilter 42 from diafiltration. It is preferred that poly(Hb) diafiltration is continued until the volume of fluid lost across ultrafilter 42 from diafiltration is about three times the initial volume of the poly(Hb) in polymerization reactor 32.

Following pH adjustment of the poly(Hb), sodium borohydride solution is added to polymerization reactor 32 through deoxygenation loop 28 to reduce imine bonds in the poly(Hb) to ketimine bonds. An acceptable range of concentrations of sodium borohydride, after initial addition of the sodium borohydride to the poly(Hb) in polymerization reactor 32, is between about 10 and 30 mM, and preferably about 15 mM to about 30 mM.

In the preferred embodiment, for every nine liters of poly(Hb) in polymerization subsystem 28, one liter of 0.25M sodium borohydride solution is added over a time period of 1 to 2 hours. A sufficient amount of sodium borohydride is added to polymerization reactor 32 through an orifice, not shown, static mixer 36 and phase membrane 38, resulting in turbulent sodium borohydride flow conditions that support rapid, effective sodium borohydride mixing with the poly(Hb) in polymerization reactor 32. During the sodium borohydride addition, the poly(Hb) in polymerization reactor 32 is continuously recirculated by pump 34 through static mixer 36 and phase transfer membrane 38 to remove dissolved oxygen and hydrogen. The flow rates of poly(Hb) and inert gas through phase transfer membrane 38 are sufficient to deoxygenate the poly(Hb). For example, when deoxygenating poly(Hb) across a 0.05µ polypropylene microfilter, flow rates of poly(Hb) and inert gas through the phase transfer membrane are typically about 2.0 to 4.0 lpm and about 12 to 18 lpm, respectively. After completion of the sodium borohydride addition, reduction continues in polymerization reactor 32 while an agitator contained therein, not shown, rotates at approximately 75 rotations per minute.

Approximately one hour after the sodium borohydride addition, the stable poly(Hb) in polymerization subsystem 28 is recirculated from polymerization reactor 32, by pump 40, through ultrafilter 42 until the Hb product concentration is about 110 g/l. Following concentration, the pH and electrolytes of the stable poly(Hb) are restored to physiologic levels, thereby forming a blood-substitute, by diafiltering the stable poly(Hb) against a filtered, deoxygenated, low pH buffer containing 27 mM sodium lactate, 12 mM NAC, 115 mM NaCl, 4 mM KCl, and 1.36 mM $CaCl_2$ in WFI, (pH 5.0). The stable poly(Hb) is diafiltered by recirculating the stable poly(Hb) from polymerization reactor 32, by pump 40, through ultrafilter 42. Diafiltration continues until the volume of fluid lost through diafiltration across ultrafilter 42 is between about 6 to about 10 times the volume of the concentrated Hb product in polymerization subsystem 38.

When intended for human use, diafiltration is typically continued until the volume of fluid lost is about 6 times the volume of the concentrated, stable poly(Hb). For veterinary blood-substitutes, the volume lost in diafiltration is about 10 times the volume of the concentrated, stable poly(Hb).

The stable polymerized hemoglobin blood-substitute produced according to the method of this invention comprises a stable poly(Hb) solution having the characteristics described in Table I.

In an embodiment where the product is intended for human use, and for some veterinary use, after the pH and electrolytes were restored to a physiologic level, thereby forming a blood-substitute, the stable polymerized Hb blood-substitute in polymerization reactor 32 is then diluted to a concentration of about 50 g/l by adding said filtered, physiologic deoxygenated low pH buffer to polymerization reactor 32. The diluted blood-substitute is then diafiltered by recirculating from polymerization reactor 32, by pump 34 through static mixer 36 and purification filter 40 against a filtered deoxygenated buffer containing 27 mM sodium lactate, 12 mM NAC, 115 mM NaCl, 4 mM KCl, and 1.36 mM $CaCl_2$ in WFI, (pH 7.8). Diafiltration continues until the blood-substitute contains less than or equal to about 10% modified tetrameric and unmodified tetrameric species by GPC when run under dissociating conditions. Purification filter 40 has a preferred molecular weight cutoff of 100,000 Daltons and is run under conditions of low transmembrane pressure with a pump restricted permeate line. The blood-substitute is then washed and equilibrated by adding a depyrogenated, deoxygenated buffer to polymerization reactor 32 and by then recirculating the blood-substitute from polymerization reactor 32, by pump 40, through ultrafilter 42. Following removal of substantial amounts of tetramer and dimer, recirculation of the blood-substitute polymerization subsystem 28 continues through ultrafilter 42 until the concentration of the blood-substitute is about 130 g/l. Examples of ultrafilters include a 30,000 MWCO membrane (Amicon 540Y30).

A stable polymerized Hb blood-substitute produced according to this method for veterinary uses typically meets the specifications provided in Table II. In addition, a stable polymerized Hb blood-substitute produced according to this method for human uses typically meets the specifications provided in Table III.

A stable polymerized Hb blood-substitute can be administered into the circulatory system of a. vertebrate by injecting the Hb blood-substitute directly and/or indirectly into the circulatory system by one or more injection methods. Examples of direct injections methods include intravascular injections, such as intravenous and intra-artepial injections, and intracardiac injections. Examples of indirect injections methods include intraperitoneal injections, subcutaneous injections, such that the Hb blood-substitute will be transported by the lymph system into the circulatory system, injections into the bone marrow by means of a trocar or catheter. Preferably, the Hb blood-substitute is administered intravenously.

The vertebrate being treated can be normovolemic or hypervolemic prior to, during, and/or after infusion of the Hb blood-substitute. The Hb blood-substitute can be directed into the circulatory system by methods such as top loading and by exchange methods.

A vertebrate is as classically defined, including humans, or any other vertebrate animals which uses blood in a circulatory system to transfer oxygen to tissue. A preferred vertebrate for the Hb blood-substitute is a mammal, such as a human, an other primate, a dog, a cat, a rat, a horse or a sheep. A vertebrate treated in the method of invention can be a fetus (prenatal vertebrate), a post-natal vertebrate, or a vertebrate at time of birth.

Pumps used in the process can include peristaltic-type, diaphragm-type, gear-type, piston-type and rotary-lobe type pumps. Diaphragm-type pumps are available from Bran & Luebbe Inc., Buffalo Grove, Ill. Suitable rotary-lobe pumps include the G&H Model 732 P51 B1 sanitary lobe-rotary pump from G&H, Renscha, Wis. Rotary-lobe pumps can also be obtained from Waukesha Pumps, Wauhesha, Wis. Peristaltic pumps can be obtained from Watson-Marlow, Inc., Wilmington, Mass.

The invention will be further illustrated by the following non-limiting examples.

EXAMPLE 1

Synthesis of Stable Polymerized Hemoglobin Blood-Substitute

As described in U.S. Pat. No. 5,296,465, samples of bovine whole blood were collected, mixed with a sodium citrate anticoagulant to form a blood solution, and then analyzed for endotoxin levels.

The term "endotoxin" refers to the cell-bound lipopolysaccharides produced as a part of the outer layer of bacterial cell walls, which under many conditions are toxic. Endotoxin unit (EU) has been defined by the United States Pharmacopeial Convention of 1983, page 3014, as the activity contained in 0.1 nanograms of U.S. reference standard lot EC-5. One vial of EC-5 contains 10,000 EU.

Each blood solution sample was maintained after collection at a temperature of about 2° C. and then strained to remove large aggregates and particles with a 600 mesh screen.

Prior to pooling, the penicillin level in each blood solution sample was assayed with an assay kit purchased from Difco, Detroit, Mich. using the method entitled "Rapid Detection of Penicillin in Milk" to ensure that penicillin levels in the blood solutions were ≦0.008 units/ml.

The blood solution samples were then pooled and mixed with depyrogenated aqueous sodium citrate solution to form a 0.2% by weight solution of sodium citrate in bovine whole blood (hereafter "0.2% sodium citrate blood solution").

The 0.2% sodium citrate blood solution was then passed, in-series, through 800μ and 50μ polypropylene filters to remove large blood solution debris of a diameter approximately 50 microns ("μ") or more.

The RBCs were then washed to separate extracellular plasma proteins, such as BSA or IgG, from the RBCs. To wash the RBCs contained in the blood solution, the volume of blood solution in the diafiltration tank was initially diluted by the addition of an equal volume of a filtered isotonic solution to diafiltration tank. The isotonic solution was filtered with a Millipore (Cat #CDUF 050 G1) 10,000 Dalton ultrafiltration membrane. The isotonic solution was composed of 6.0 g/l sodium citrate dihydrate and 8.0 g/l sodium chloride in water-for-injection (WFI). The term WFI is described in *Pharmaceutical Engineering*, 11, 15–23 (1991).

The diluted blood solution was then concentrated back to its original volume by diafiltration through a 0.2 μm hollow fiber (Microgon Krosflo II microfiltration cartridge) diafilter. Concurrently, filtered isotonic solution was added continuously, as makeup, at a rate equal to the rate of filtrate loss through the 0.2 μm diafilter. During diafiltration, components of the diluted blood solution which were signifi-cantly smaller in diameter than RBCs, or are fluids such as plasma, passed through the walls of the 0.2 μm diafilter with the filtrate. RBCs, platelets and larger bodies of the diluted blood solution, such as white blood cells, were retained with continuously-added isotonic solution to form a dialyzed blood solution.

During RBC washing, the diluted blood solution was maintained at a temperature between approximately 10° C. to 25° C. with a fluid pressure at the inlet of the diafilter between about 25 and 30 psi.

RBC washing was complete when the volume of filtrate drained from the diafilter equaled about 600% of the volume of blood solution prior to diluting with filtered isotonic solution.

The dialyzed blood solution was then continuously pumped at a rate of approximately 4 lpm to a Sharples Super Centrifuge, Model #AS-16, fitted with a #28 ringdam. The centrifuge was operating while concurrently being fed dialyzed blood solution, to separate the RBCs from the white blood cells and platelets. During operation, the centrifuge rotated at a rate sufficient to separate the RBCs into a heavy RBC phase, while also separating a substantial portion of the white blood cells (WBCs) and platelets into a light WBC phase, specifically about 15,000 rpm. A fraction of the RBC phase and of the WBC phase were separately and continuously discharged from the centrifuge during operation.

Following separation of the RBCs, the RBCs were lysed to form a hemoglobin-containing solution. A substantial portion of the RBCs were mechanically lysed while discharging the RBCs from the centrifuge. The cell membranes of the RBCs ruptured upon impacting the wall of RBC phase discharge line at an angle to the flow of RBC phase out of the centrifuge, thereby releasing hemoglobin (Hb) from the RBCs into the RBC phase.

The lysed RBC phase then flowed through the RBC phase discharge line into a static mixer (Kenics ½ inch with 6 elements, Chemineer, Inc.). Concurrent with the transfer of the RBC phase to the static mixer, an equal amount of WFI was also injected into the static mixer, wherein the WFI mixed with the RBC phase. The flow rates of the RBC phase and the WFI into static mixer 40 are each at about 0.25 lpm.

Mixing the RBC phase with WFI in the static mixer produced a lysed RBC colloid. The lysed RBC colloid was then transferred from the static mixer into a Sharples Super Centrifuge (Model #AS-16, Sharples Division of Alfa-Laval Separation, Inc.) which was suitable to separate the Hb from nonhemoglobin RBC components. The centrifuge was rotated at a rate sufficient to separate the lysed RBC colloid into a light Hb phase and a heavy phase. The light phase was composed of Hb and also contained non-hemoglobin components with a density approximately equal to or less than the density of Hb.

The Hb phase was continuously discharged from the centrifuge, through a 0.45μ Millipore Pellicon Cassette, Cat #HVLP 000 C5 microfilter, and into a holding tank in preparation for Hb purification. Cell stroma when then returned with the retentate from the microfilter to the holding tank. During microfiltration, the temperature within the holding tank was maintained at 10° C. or less. When the fluid pressure at the microfilter inlet increased from an initial pressure of about 10 psi to about 25 psi, microfiltration was complete. The Hb microfiltrate was then transferred from the microfilter into the microfiltrate tank.

Subsequently, the Hb microfiltrate was pumped through a 100,000 Millipore Cat #CDUF 050 H1 ultrafilter. A substantial portion of the Hb and water, contained in the Hb microfiltrate, permeated the 100 kD ultrafilter to form a Hb ultrafiltrate, while larger cell debris, such as proteins with a molecular weight above about 100 kD, were retained and recirculated back into the microfiltrate tank. Concurrently, WFI was continuously added to the microfiltrate tank as makeup for water lost in the ultrafiltrate. Generally, cell debris include all whole and fragmented cellular components with the exception of Hb, smaller cell proteins, electrolytes, protein aggregates, coenzymes and organic metabolic intermediates. Ultrafiltration continued until the concentration of Hb in the microfiltrate tank was less than 8 grams/liter (g/l). While ultrafiltering the Hb, the internal temperature of the microfiltrate tank was maintained at about 10° C.

The Hb ultrafiltrate was transferred into an ultrafiltrate tank, wherein the Hb ultrafiltrate was then recirculated through a 30,000 Millipore Cat #CDUF 050 T1 ultrafilter to remove smaller cell components, such as electrolytes, coenzymes, metabolic intermediates and proteins less than about 30,000 Daltons in molecular weight, and water from the Hb ultrafiltrate, thereby forming a concentrated Hb solution containing about 100 g Hb/l.

The concentrated Hb solution was then directed from the ultrafiltrate tank onto the media contained in parallel chromatographic columns (2 feet long with an 8 inch inner diameter) to separate the Hb by high performance liquid chromatography. The chromatographic columns contained an anion exchange medium suitable to separate Hb from nonhemoglobin proteins. The anion exchange media was formed from silica gel. The silica gel was exposed to γ-glycidoxy propylsilane to form active epoxide groups and then exposed to $C_3H_7(CH_3)NCl$ to form a quaternary ammonium anion exchange medium. This method of treating silica gel is described in the *Journal of Chromatography*, 120:321–333 (1976).

Each column was pre-treated by flushing the chromatographic columns with a first buffer which facilitated Hb binding. Then 4.52 liters of the concentrated Hb solution were injected into each chromatographic column. After injecting the concentrated Hb solution, the chromatographic columns were then washed by successively directing three different buffers through the chromatographic columns to produce a Hb elute, by producing a pH gradient within the columns. The temperature of each buffer was about 12.4° C. The buffers were prefiltered through a 10,000 Dalton ultrafiltration membrane before injection onto the chromatographic columns.

The first buffer, 20 mM tris-hydroxymethyl aminomethane (Tris) (pH about 8.4 to about 9.4), transported the concentrated Hb solution into the media in the chromatographic columns to bind the Hb. The second buffer, a mixture of the first buffer and a third buffer, with the second buffer having a pH of about 8.3, then adjusted the pH within chromatographic columns to elute contaminating non-hemoglobin components from the chromatographic columns, while retaining the Hb. Equilibration with the second buffer continued for about 30 minutes at a flow rate of approximately 3.56 lpm per column. The elute from the second buffer was discarded to waste. The third buffer, 50 mM Tris (pH about 6.5 to about 7.5), then eluted the Hb from the chromatographic columns.

The Hb elute was then directed through a 0.22 μmeter Sartorius cartridge filter (#5232507 G1PH) to a tank wherein the Hb elute was collected. The first 3-to-4% of the Hb elute and the last 3-to-4% of the Hb elute were directed to waste.

The Hb elute was further used if the elute contained less than 0.5 Eu/ml of endotoxin and contained less than 3.3 nM/ml phospholipids. To sixty liters of ultrapure elute, which had a concentration of 100 g Hb/l, was added 9 liters of 1.0M NaCl, 20 mM Tris (pH 8.9) buffer, thereby forming a Hb solution with an ionic strength of 160 mOsm, to reduce the oxygen affinity of the Hb in the Hb solution. The Hb solution was then concentrated at 10° C., by recirculating through the ultrafilter, specifically a 10,000 Dalton Millipore Helicon, Cat #CDUF050G1 filter, until the Hb concentration was 110 g/l.

The Hb solution was then deoxygenated, until the $pO_2$ of the Hb solution was reduced to the level where $HbO_2$ content was about 10%, by recirculating the Hb solution at 12 lpm, through a 0.05μ Hoechst-Celanese Corporation Cat #G-240/40) polypropylene microfilter phase transfer membrane, to form a deoxygenated Hb solution (hereinafter "deoxy-Hb"). Concurrently, a 60 lpm flow of nitrogen gas was directed through the counter side of the phase transfer membrane. During deoxygenation, temperature of the Hb solution was maintained between about 19° C. and about 31° C.

Also during deoxygenation, and subsequently throughout the process, the Hb was maintained in a low oxygen environment to minimize oxygen absorption by the Hb and to maintain an oxygenated Hb (oxyhemoglobin or $HbO_2$) content of less than about 10% in the deoxy-Hb.

The deoxy-Hb was then diafiltered through an ultrafilter with 180 liters of a storage buffer, containing 0.2 wt % N-acetyl cysteine, 33 mM sodium phosphate buffer (pH 7.8) having a $pO_2$ of less than 50 torr $pO_2$, to form an oxidation-stabilized deoxy-Hb. Prior to mixing with the deoxy-Hb, the storage buffer was depyrogenated with a 10,000 Dalton Millipore Helicon, Cat #CDUF050G1 depyrogenating filter. The storage buffer was continuously added at a rate approximately equivalent to the fluid loss across the ultrafilter. Diafiltration continued until the volume of fluid lost through diafiltration across the ultrafilter was about three times the initial volume of the deoxy-Hb.

Prior to transferring the oxidation-stabilized deoxy-Hb into a polymerization apparatus, oxygen-depleted WFI was added to the polymerization reactor to purge the polymerization apparatus of oxygen to prevent oxygenation of oxidation-stabilized deoxy-Hb. The amount of WFI added to the polymerization apparatus was that amount which would result in a Hb solution with a concentration of about 40 g Hb/l, when the oxidation-stabilized deoxy-Hb was added to the polymerization reactor. The WFI was then recirculated throughout the polymerization apparatus and deoxygenated by flowing through a 0.05μ polypropylene microfilter phase transfer membrane (Hoechst-Celanese Corporation Cat #G240/40, 40 sq. ft.) against a counterflow of a pressurized nitrogen. The flow rates of WFI and nitrogen gas, through the phase transfer membrane, were about 18 to 20 lpm and 40 to 60 lpm, respectively.

After the $pO_2$ of the WFI in polymerization apparatus was reduced to less than about 2 torr $pO_2$, the polymerization reactor was blanketed with nitrogen by a flow of about 20 lpm of nitrogen into the head space of the polymerization reactor. The oxidation-stabilized deoxy-Hb was then transferred into the polymerization reactor.

The polymerization was conducted in a 12 mM phosphate buffer with a pH of 7.8, having a chloride concentration less than or equal to about 35 mmolar.

The oxidation-stabilized deoxy-Hb and N-acetyl cysteine were subsequently slowly mixed with the cross-linking agent glutaraldehyde, specifically 29.4 grams of glutaraldehyde for each kilogram of Hb over a five hour period, while heating at 42° C. and recirculating the Hb solution through a Kenics 1-½ inch static mixer with 6 elements (Chemineer, Inc.), to form a polymerized Hb solution (hereinafter "poly(Hb)").

Recirculating the oxidation-stabilized deoxy-Hb and the glutaraldehyde through the static mixer at a flow rate of 25–40 lpm caused turbulent flow conditions with generally uniform mixing of the glutaraldehyde with the oxidation-stabilized deoxy-Hb, thereby reducing the potential for forming pockets of deoxy-Hb containing high concentrations of glutaraldehyde. Generally, uniform mixing of glutaraldehyde and deoxy-Hb reduced the formation of high molecular weight poly(Hb) (having a molecular weight above 500,000 Daltons) and also permitted faster mixing of glutaraldehyde and deoxy-Hb during polymerization.

In addition, significant Hb intramolecular cross-linking resulted during Hb polymerization as an effect of the presence of N-acetyl cysteine upon the polymerization of Hb.

After polymerization, the temperature of the poly(Hb) in the polymerization reactor was reduced to a temperature between about 18° C. to about 22° C.

The poly(Hb) was then concentrated by recirculating the poly(Hb) through the ultrafilter until the concentration of the poly(Hb) was increased to about 85 g/l. A suitable ultrafilter is a 30,000 Dalton filter (e.g., Millipore Helicon, Cat #CDUF050LT).

Subsequently, the poly(Hb) solution was then mixed with 66.75 g sodium borohydride, to the poly(Hb) and then again recirculated through the static mixer at a flow rate of 10–20 lpm. Specifically, for every nine liters of poly(Hb), one liter of 0.25M sodium borohydride solution was added.

Prior to adding the sodium borohydride to the poly(Hb), the pH of the poly(Hb) was basified by adjusting pH to a pH of about 10 to preserve the sodium borohydride and to prevent hydrogen gas formation, which can denature proteins during reduction. The pH of the poly(Hb) was adjusted by diafiltering the poly(Hb) with approximately 215 liters of depyrogenated, deoxygenated 12 mM sodium borate buffer, having a pH of about 10.4 to about 10.6. The poly(Hb) was diafiltered by recirculating the poly(Hb) from the polymerization reactor through the 30 kD ultrafilter. The sodium borate buffer was added to the poly(Hb) at a rate approximately equivalent to the rate of fluid loss across the ultrafilter from diafiltration. Diafiltration continued until the volume of fluid lost across the ultrafilter from diafiltration was about three times the initial volume of the poly(Hb) in the polymerization reactor.

Following pH adjustment, sodium borohydride solution was added to the polymerization reactor to form stable poly(Hb). During the sodium borohydride addition, the poly(Hb) in the polymerization reactor was continuously recirculated through the static mixer and the 0.05 g polypropylene microfilter phase transfer membrane to remove dissolved oxygen and hydrogen. Flow through a static mixer also provided turbulent sodium borohydride flow conditions that rapidly and effectively mixed sodium borohydride with the poly(Hb). The flow rates of poly(Hb) and nitrogen gas through the 0.05μ phase transfer membrane were between about 2.0 to 4.0 lpm and about 12 to 18 lpm, respectively. After completion of the sodium borohydride addition, reduction continued in the polymerization reactor while an agitator contained therein rotated at approximately 75 rotations per minute.

Approximately one hour after the sodium borohydride addition, the stable poly(Hb) was recirculated from the polymerization reactor through the 30 kD ultrafilter until the Hb product concentration was about 110 g/l. Following concentration, the pH and electrolytes of the stable poly(Hb) were restored to physiologic levels to form a stable polymerized Hb blood-substitute, by diafiltering the stable poly(Hb), through the 30 kD ultrafilter, with a filtered, deoxygenated, low pH buffer containing 27 mM sodium lactate, 12 mM NAC, 115 mM NaCl, 4 mM KCl, and 1.36 mM $CaCl_2$ in WFI, (pH 5.0). Diafiltration continued until the volume of fluid lost through diafiltration across the ultrafilter was about 6 times the pre-diafiltration volume of the concentrated Hb product.

After the pH and electrolytes were restored to physiologic levels, the stable polymerized Hb blood-substitute was then diluted to a concentration of 50 g/l by adding the filtered, deoxygenated low pH buffer to the polymerization reactor. The diluted blood-substitute was then diafiltered by recirculating from the polymerization reactor through the static mixer and a 100 kD purification filter against a filtered deoxygenated buffer containing 27 mM sodium lactate, 12 mM NAC, 115 mM NaCl, 4 mM KCl, and 1.36 mM $CaCl_2$ in WFI, (pH 7.8). Diafiltration continued until the blood-substitute contained less than or equal to about 10% modified tetrameric and unmodified tetrameric species by GPC when run under dissociating conditions.

Suitable membranes include a Filtron Omega polysulfone membrane (Cta. #OS100COS).

Modified tetrameric Hb is defined as tetrameric Hb which has been intramolecularly cross-linked to preclude significant dissociation of the Hb tetramers into Hb dimers.

The purification filter was run under conditions of low transmembrane pressure with a restricted permeate line. Following removal of substantial amounts of modified tetrameric Hb and unmodified tetrameric Hb, recirculation of the blood-substitute continued through the 30 kD ultrafilter until the concentration of the blood-substitute was about 130 g/l.

The stable blood-substitute was then stored in a suitable container having a low oxygen environment and a low oxygen in-leakage.

EXAMPLE 2

Polymerized Hemoglobin Analysis

The endotoxin concentration in the hemoglobin product is determined by the method "Kinetic/Turbidimetric LAL 5000 Methodology" developed by Associates of Cape Cod, Woods Hole, Mass., J. Levin et al., *J. Lab. Clin. Med.*, 75:903–911 (1970). Various methods were used to test for any traces of stroma for example, a precipitation assay, Immunoblotting, and enzyme-linked immunosorbent assay (ELISA) for a specific cell membrane protein or glycolipid known by those skilled in the art.

Particulate counting was determined by the method "Particulate Matter in Injections: Large Volume Injections for Single Dose Infusions", U.S. Pharmacopeia 22:1596, 1990.

To determine glutaraldehyde concentration, a 400 μl representative sample of the hemoglobin product was derivitized with dinitrophenylhydrazine and then a 100 μl aliquot of the derivative solution was injected onto a YMC AQ-303 ODS column at 27° C., at a rate of 1 ml/min., along with a gradient. The gradient consisted of two mobile phases, 0.1% trifluoroacetic acid (TFA) in water and 0.08% TFA in acetonitrile. The gradient flow consisted of a constant 60% 0.08% TFA in acetonitrile for 6.0 minutes, a linear gradient to 85% 0.08% TFA in acetonitrile over 12 minutes, a linear gradient to 100% 0.08% TFA in acetonitrile over 4 minutes hold at 100% 0.08% TFA in acetonitrile for 2 minutes and re-equilibrate at 45% 0.1% TFA in water. Ultraviolet detection was measured at @360 nm.

To determine N-acetyl cysteine concentration, an aliquot of hemoglobin product was diluted 1:100 with degassed sodium phosphate in water and 50 μl was injected onto a YMC AQ-303 ODS column with a gradient. The gradient buffers consisted of a sodium phosphate in water solution and a mixture of 80% acetonitrile in water with 0.05% TFA. The gradient flow consisted of 100% sodium phosphate in water for 15 minutes, then a linear gradient to 100% mixture of 80% acetonitrile and 0.05% TFA over 5 minutes, with a hold for 5 minutes. The system was then re-equilibrated at 100% sodium phosphate for 20 minutes.

Phospholipid analysis was done by a method based on procedures contained in the following two papers: Kolarovic et al., "A Comparison of Extraction Methods for the Isolation of Phospholipids from Biological Sources", *Anal. Biochem.*, 156:244–250, 1986 and Duck-Chong, C. G., "A Rapid Sensitive Method for Determining Phospholipid Phosphorus Involving Digestion With Magnesium Nitrate", *Lipids*, 14:492–497, 1979.

Osmolarity was determined by analysis on an Advanced Cryomatic Osmometer, Model #3C2, Advanced Instruments, Inc., Needham, Mass.

Total hemoglobin, methemoglobin and oxyhemoglobin concentrations were determined on a Co-Oximeter Model #482, from Instrumentation Laboratory, Lexington, Mass.

$Na^+$, $K^+$, $Cl^-$, $Ca^{++}$, $pO^2$ concentrations were determined by a Novastat Profile 4, Nova Biomedical Corporation, Waltham, Mass.

Oxygen binding constant, $P_{50}$ was determined by a Hemox-Analyzer, TCS Corporation, Southhampton, Pa.

Temperature and pH were determined by standard methods known by those skilled in the art.

Molecular weight (M.W.) was determined by conducting high performance size exclusion chromatography on the hemoglobin products under dissociating conditions. A representative sample of the hemoglobin product was analyzed for molecular weight distribution. The hemoglobin product was diluted to 4 mg/ml within a mobile phase buffer of 50 mM Bis-Tris (pH 6.5), 750 mM $MgCl_2$, and 0.1 mM EDTA. This buffer serves to dissociate Hb tetramer into dimers, that have not been cross-linked to other Hb dimers through intramolecular or intermolecular cross-links, from the poly-Hb. The diluted sample was injected onto a TosoHaas G3000SW column. Flow rate was 0.5 ml/min. and ultraviolet detection was recorded at 280 nm.

Analysis of the resulting polymerized Hb solution found that 96% or more of the hemoglobin molecules were intermolecularly and/or intramolecularly cross-linked, with 28–33% of the poly(Hb) being in a intramolecularly cross-linked tetrameric form and about 4–7% of the poly(Hb) had a molecular weight greater than 500,000 Daltons. Furthermore, analysis of the blood-substitute found that it met all specifications for veterinary blood-substitute provided in Table II.

In addition, evaluation of the blood-substitute, produced according to this method, showed that the blood-substitute also satisfactorily met a general safety test. In the general safety test, 2 mice and 2 guinea pigs were injected with blood-substitute, after which the test animals were monitored for 7 days. None of the animals injected with blood-substitute experienced a weight gain, a weight loss or death, thereby demonstrating the general safety of the blood-substitute.

EXAMPLE 3

Stability Analysis of Stable Polymerized Hemoglobin Blood-Substitute

The stability of polymerized hemoglobin blood-substitute, produced according to the method of this invention, was evaluated over a period of 24 months at various storage temperatures. The specific storage temperatures evaluated were 2–8° C., room temperature (about 25° C.) and 37° C. For storage at 2–8° C. and at room temperature (RT), the stability results (provided in Table IV) show that the blood-substitute was stable for two years with only de minimis changes in the composition of the blood-substitute. Further, for storage at 37° C., the blood-substitute was stable for over one year. Blood-substitute stored at 37° C. for 18 months, however, showed , 5 particles/ml at 25μ and more than 11% Hb with a molecular weight greater than 500,000 Daltons.

In these analyses, total hemoglobin, methemoglobin and oxyhemoglobin concentrations were determined on a Co-Oximeter Model #482, from Instrumentation Laboratory, Lexington, Mass.

TABLE IV

| Test and Specification | Initial | 24-Month Storage at 2–8° C. | 24-Month Storage at RT | 12-Month Storage at 37° C. |
|---|---|---|---|---|
| Package Integrity | Meets Test | Meets Test | Meets Test | Meets Test |
| Total Hb 13 ± 1 g/dl | 12.6 | 12.8 | 12.8 | 12.8 |
| MetHb 10% | 3.1 | 1.8 | 2.0 | 1.4 |
| Glutaraldehyde < 3.5 g/ml | N.D. | 0.03 | 0.03 | 0.01 |
| NAC ≦ 0.2% | 0.14 | 0.18 | 0.15 | 0.13 |
| Particulate Content < 50/ml at ≧10 μ | Pass | Pass | Pass | Pass |
| <5/ml at ≧25 μ | Pass | Pass | Pass | Pass |
| Deep Purple Color | Pass | Pass | Pass | Pass |
| pH 7.6–7.9 | 7.8 | 7.8 | 7.8 | 7.8 |
| $HbO_2$ ≦ 10% | 4.5 | 2.3 | 2.3 | 3.1 |
| Osmolarity 290–310 mOsm | 303 | 298 | 300 | 299 |
| Molecular Weight >500 kD ≦ 10% | 7.1 | 9.16 | 9.84 | 9.30 |
| <32 kD ≦ 5% | 2.9 | 2.86 | 3.00 | 3.26 |

N.D. means not determined.

In addition, molecular weight was determined by conducting high performance size exclusion chromatography (HPSEC) on the blood-substitute. A representative sample of the blood-substitute was analyzed for molecular weight distribution. The hemoglobin product was diluted to 4 mg/ml within a mobile phase of 50 mM Bis-Tris (pH 6.5), 750 mM $MgCl_2$, and 0.1 mM EDTA. The diluted sample was injected onto a HPLC TosoHaas G3000SW column. Flow rate was 0.5 mL/minute and ultraviolet detection was set at @280 nm.

Package integrity was evaluated by performing a visual inspection of the packages, containing the blood-substitute, for leaks.

Equivalents

Those skilled in the art will recognize, or be able to ascertain using no more than routine experimentation, many equivalents to the specific embodiments of the invention described herein. These and all other such equivalents are intended to be encompassed by the following claims.

The invention claimed is:

1. A method for producing a polymerized hemoglobin solution, useful for forming a stable blood-substitute, from hemoglobin contained in a hemoglobin solution, comprising the steps of:
   a) deoxygenating said hemoglobin solution;
   b) mixing said deoxygenated hemoglobin solution with a sulfhydryl compound selected from the group consisting of N-acetyl-L-cysteine, D,L-cysteine, glutathione, γ-glutamyl-cysteine, 2,3-dimercapto-1-propanol, thioglycolate, and 1,4-butanedithiol, to form a solution of the sulfhydryl compound and said hemoglobin;
   c) mixing said solution of sulfhydryl compound and hemoglobin with a cross-linking agent to form a polymerization reaction mixture; and
   d) polymerizing the polymerization reaction mixture, thereby forming a polymerized hemoglobin solution.

2. A method of claim 1 wherein said hemoglobin solution comprises mammalian hemoglobin.

3. A method of claim 1 wherein said mammalian hemoglobin solution is formed from hemoglobin selected from a group consisting of human hemoglobin, bovine hemoglobin, ovine hemoglobin, porcine hemoglobin.

4. A method of claim 1 wherein the deoxygenated hemoglobin solution has an oxyhemoglobin content of less than about ten percent.

5. A method of claim 1 wherein said sulfhydryl compound comprises N-acetyl-L-cysteine.

6. A method of claim 1 wherein the oxidation-stabilized, deoxygenated hemoglobin solution and the cross-linking agent are mixed under low shear conditions.

7. A method of claim 1 wherein the cross-linking agent comprises a polyfunctional agent.

8. A method of claim 7 wherein the polyfunctional agent comprises a dialdehyde.

9. A method of claim 8 wherein the dialdehyde comprises glutaraldehyde.

10. A method of claim 7 wherein the polymerized hemoglobin contains unstable bonds, further comprising the steps of:
    a) contacting the polymerized hemoglobin solution with an alkaline solution, whereby the polymerized hemoglobin solution is basified; and
    b) contacting the basified polymerized hemoglobin solution with a reducing agent, whereby unstable bonds are reduced, thereby forming a stable polymerized hemoglobin solution.

11. A method of claim 10 wherein said reducing agent comprises sodium borohydride.

12. A method for producing a stable polymerized hemoglobin blood-substitute from mammalian hemoglobin in a hemoglobin solution, comprising the steps of:
    a) deoxygenating the mammalian hemoglobin solution, whereby the oxyhemoglobin content of the hemoglobin solution is reduced to less than about ten percent;
    b) mixing the deoxygenated hemoglobin solution with a sulfhydryl compound selected from the group consisting of N-acetyl-L-cysteine, D,L-cysteine glutathione, γ-glutamyl-cysteine, 2,3-dimercapto-1-propanol, thioglycolate, and 1,4-butanedithiol, to form a solution of the sulfhydryl compound and said hemoglobin;
    c) mixing said solution of sulfhydryl compound and hemoglobin with a dialdehyde to form a polymerization reaction mixture;
    d) heating the polymerization reaction mixture, whereby a polymerized hemoglobin solution is formed;
    e) contacting the polymerized hemoglobin solution with an alkaline solution, whereby the polymerized hemoglobin solution is basified;
    f) contacting the basified polymerized hemoglobin solution with a reducing agent, whereby a stable polymerized hemoglobin solution is formed; and
    g) diafiltering the stable polymerized hemoglobin solution with a first physiologic solution, having a pH of 7.9 or lower, whereby the stable polymerized hemoglobin solution is made physiologically acceptable, thereby forming said stable polymerized hemoglobin blood-substitute.

13. A method of claim 12 for making a human blood-substitute, further comprising the step of diafiltering the stable polymerized hemoglobin blood-substitute with a second physiologic solution, having a pH between 7.6 and 7.9, against a filter suitable to separate non-polymerized hemoglobin from polymerized hemoglobin, thereby forming a human blood-substitute.

14. A method of claim 13 wherein the first physiologic solution and the second physiologic solution are the same.

15. A method of claim 13 wherein the first physiologic solution is acidic.

16. A method for producing a stable polymerized hemoglobin human blood-substitute from bovine hemoglobin in a hemoglobin solution, comprising the steps of:
    a) deoxygenating the bovine hemoglobin solution, whereby the oxyhemoglobin content of the hemoglobin solution is reduced to less than about ten percent;
    b) mixing the deoxygenated hemoglobin solution with N-acetyl-L-cysteine, whereby the deoxygenated hemoglobin solution is oxidation-stabilized;
    c) mixing the oxidation-stabilized hemoglobin solution with glutaraldehyde to form a polymerization reaction mixture;
    d) heating the polymerization reaction mixture, whereby a polymerized hemoglobin solution is formed;
    e) contacting the polymerized hemoglobin solution with an alkaline borate buffer, whereby the polymerized hemoglobin solution is basified;
    f) contacting the basified polymerized hemoglobin solution with a sodium borohydride, whereby unstable imine bonds are reduced, whereby a stable polymerized hemoglobin solution is formed;
    g) diafiltering the stable polymerized hemoglobin solution with a first physiologic solution, containing 27 mM sodium lactate, 12 mM NAC, 115 mM NaCl, 4 mM KCl, and 1.36 mM $CaCl_2$ and having a pH of about 5, whereby the stable polymerized hemoglobin solution is made physiologically acceptable, thereby forming said stable polymerized hemoglobin blood-substitute; and
    h) diafiltering the stable polymerized hemoglobin blood-substitute with a second physiologic solution, containing 27 mM sodium lactate, 12 mM NAC, 115 mM NaCl, 4 mM KCl, and 1.36 mM $CaCl_2$ and having a pH of about 7.8, against a filter suitable to separate non-polymerized hemoglobin from polymerized hemoglobin, thereby forming a human blood-substitute.

17. A method for producing a polymerized hemoglobin solution, used to form a stable blood-substitute, from hemoglobin contained in a hemoglobin solution, comprising the steps of:

a) deoxygenating said hemoglobin solution;

b) mixing said deoxygenated hemoglobin solution with a cross-linking agent and a sulfhydryl compound selected from the group consisting of N-acetyl-L-cysteine, D,L-cysteine, glutathione, γ-glutamyl-cysteine, 2,3-dimercapto-1-propanol, thioglycolate, and 1,4-butanedithiol, to form a polymerization reaction mixture; and c) heating the polymerization reaction mixture, thereby forming a polymerized hemoglobin solution.

18. A method for producing a stable polymerized hemoglobin solution, from hemoglobin in a hemoglobin solution, comprising the steps of:

a) mixing the hemoglobin solution with a sulfhydryl compound selected from the group consisting of N-acetyl-L-cysteine, D,L-cysteine, glutathione, γ-glutamyl-cysteine, 2,3-dimercapto-1-propanol, thioglycolate, and 1,4-butanedithiol, whereby the hemoglobin solution is deoxygenated and forms an oxidation-stabilized, deoxygenated hemoglobin solution; and b) mixing said deoxygenated hemoglobin solution with a cross-linking agent to form said stable polymerized hemoglobin solution.

19. The method of claim 5, wherein the solution of sulfhydryl compound and hemoglobin includes from about 0.003% to about 0.3% N-acetyl-L-cysteine by weight.

20. The method of claim 19, wherein the solution of sulfhydryl compound and hemoglobin includes from about 0.05% to about 0.2% N-acetyl-L-cysteine by weight.

21. The method of claim 12, wherein the sulfhydryl compound comprises N-acetyl-L-cysteine.

22. The method of claim 21, wherein the solution of sulfhydryl compound and hemoglobin includes from about 0.003% to about 0.3% N-acetyl-L-cysteine by weight.

23. The method of claim 22, wherein the solution of sulfhydryl compound and hemoglobin includes from about 0.05% to about 0.2% N-acetyl-L-cysteine by weight.

24. The method of claim 1, wherein the deoxygenated hemoglobin solution has a concentration of hemoglobin in a range of between about 3.7 and about 4.4 gm/dl.

* * * * *